United States Patent [19]

Hauptli

[11] Patent Number: 5,394,201
[45] Date of Patent: Feb. 28, 1995

[54] BINOCULAR OPHTHALMOSCOPE WITH MIRROR ADJUSTMENT

[75] Inventor: Ronald A. Hauptli, Warners, N.Y.

[73] Assignee: Welch Allyn, Inc., Skaneateles Falls, N.Y.

[21] Appl. No.: 109,078

[22] Filed: Aug. 19, 1993

[51] Int. Cl.⁶ .................. A61B 3/10; G02B 27/02
[52] U.S. Cl. .................. 351/221; 351/205; 351/246; 359/482
[58] Field of Search .............. 351/200, 205, 211, 216, 351/221, 245, 156, 206, 246; 359/407, 471, 482

[56] References Cited

U.S. PATENT DOCUMENTS

| | | | |
|---|---|---|---|
| 4,449,797 | 5/1984 | Kocher et al. | 351/205 |
| 4,568,158 | 2/1986 | Blaha et al. | 351/205 |
| 4,684,227 | 8/1987 | Schmidt et al. | 351/205 |
| 4,710,002 | 12/1987 | Pomerantzeff | 351/205 |
| 4,810,083 | 3/1989 | Okada et al. | 351/205 |
| 5,223,863 | 6/1993 | Heine et al. | 351/205 |

*Primary Examiner*—William L. Sikes
*Assistant Examiner*—David R. Parsons
*Attorney, Agent, or Firm*—Harris Beach & Wilcox

[57] ABSTRACT

A binocular ophthalmoscope having a pair of eyepieces that are mounted in a frame and arranged to view a target area in the eye through a pair of angularly offset reflecting surfaces. The reflecting surfaces are seated on a carriage that is mounted for reciprocation in the frame. A mirror is pivotally mounted in the frame and arranged to direct a beam of light at the target area. A camming mechanism connects the mirror and the carriage so that the axis of the light beam and the axes of the image paths to the reflecting surfaces all move closer together as the carriage moves in one direction and moves further apart as the carriage moves in the opposite direction.

12 Claims, 7 Drawing Sheets

BINOCULAR OPHTHALMOSCOPE WITH MIRROR ADJUSTMENT

BACKGROUND OF THE INVENTION

This invention relates to a binocular ophthalmoscope and, in particular, to a binocular ophthalmoscope having an improved control mechanism for simultaneously adjusting the light beam used to illuminate a patient's eye and the two stereoscopic image paths reflected back from the patient's eye to the Examiner's eyes.

It is important for a physician examining the interior of a patient's eye to have a clear field of vision into the eye while at the same time providing sufficient illumination of the object so that effective diagnosis of the condition of the eye can be accomplished. The binocular ophthalmoscope utilizes two reflected image paths to produce a stereoscopic image presentation of the inner eye. Simultaneously, illumination from a light source must be passed into the eye through the pupil without interfering with image information coming back to the examiner. In effect, the two viewing axes and the light axis must be able to pass through the pupil without interference.

Attempts to adjust the two image axes and the light axis to accommodate a specific pupil size has heretofore been a difficult task, requiring the physician to make a number of separate adjustments to the optical and illumination systems. This becomes all the more difficult where the instrument is suspended from a head band encircling the examiner's head. Heine et. al. in U.S. Pat. Nos. 4,684,227 and 5,223,863 has, to some extent, alleviated this difficulty by mounting a pair of image reflecting mirrors and an illumination mirror on a common platform that can be moved toward and away from the object being viewed. The image reflecting mirrors are placed at right angles upon the platform with the apex of the right angle corner facing the target. Reflected images from the mirrors are directed into opposed eye pieces for viewing. As the platform is moved toward the target, the reflected image axes are moved apart and conversely as the platform is moved back from the target, the image axes come closer together. An illumination mirror is also mounted at the right angle corner formed by the two imager mirrors and serves to direct light from a fixed source onto the target. The light axis of the redirected illumination beam is also shifted in relation to the movement of the platform to bring the light axis closer to the image axes as the platform is moved back from the object and to spread the axes apart as the platform is moved back from the target.

As can be seen, adjustment of the Heine et. al. instrument can be accomplished by simply moving the platform which supports the lighting mirror and the imaging mirrors. While the single control platform simplifies the adjustment of the instrument to accommodate various size pupils, the light reflecting mirrors block a good deal of the otherwise usable surface area of the image mirrors and thus places serious limitations on the viewing range of the instrument. By the same token, the tilt of the illumination mirror described in the U.S. Pat. No. 4,684,227 patent is fixed and thus the examining physician cannot finely adjust the illumination beam.

SUMMARY OF THE INVENTION

It is therefore an object of the present invention to improve binocular ophthalmoscopes.

It is another object of the present invention to provide a binocular ophthalmoscope that is easily adjustable and has an unobstructed view of a patient's inner eye.

A still further object of the present invention is to provide a binocular ophthalmoscope that allows optimization of the degree of stereopsis and view of the patient's eye without reflex or parallax regardless of the pupil size.

Another object of the present invention is to provide an easily adjustable binocular ophthalmoscope that further permits fine adjustment of the illumination beam without interfering with the view through the instrument.

These and other objects of the present invention are attained by means of a binocular ophthalmoscope used to view objects inside the eye that includes a frame having a pair of opposed eyepieces mounted therein, a light source mounted in the frame, a carriage movably mounted in the frame toward and away from the eye, angularly offset reflecting surfaces mounted upon the carriage for bringing a reflected image of an object to each eyepiece along separate image paths, the mirrors being positioned on the carriage so that the distance between the image paths increases as the carriage is moved toward the target eye and decreases as the carriage moves away from the target eye. A tiltable mirror is mounted above the carriage for directing a light beam from the source into the eye. A control mechanism that is responsive to the movement of the carriage adjusts the position of the mirror to increase the distance between the axis light beam and the axes of the two image paths when the carriage is moved toward the target eye and decreases the distance therebetween when the carriage is moved away from the target eye. A further adjustment is provided which enables the examiner to preset the illuminating light beam entering the eye at a desired angle for maximum illumination. This preset angle is maintained when the relative positioning of the light beam axis and the reflected image path axes are adjusted through the control mechanism.

BRIEF DESCRIPTION OF THE DRAWINGS

For a better understanding of these and other objects of the present invention reference shall be made to the following detailed description of the invention which is to be read in association with the accompanying drawings wherein.

DETAILED DESCRIPTION OF A PREFERRED EMBODIMENT

Figure 1:
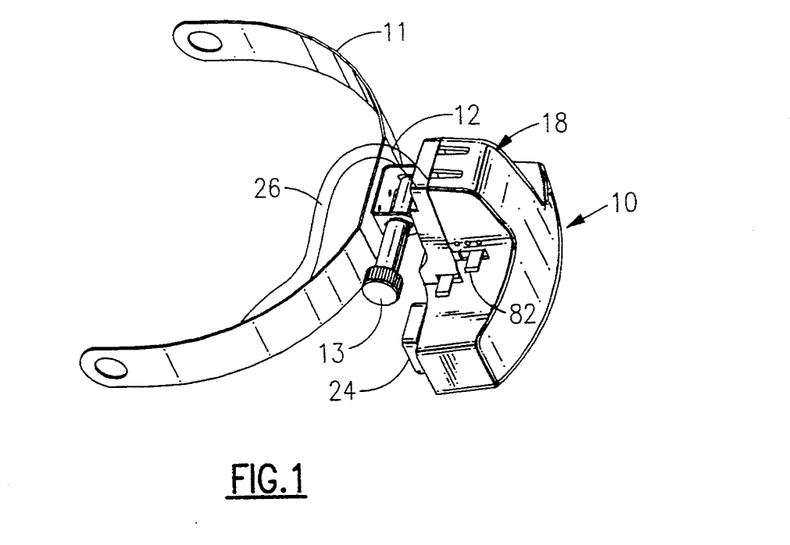
FIG. 1 is a perspective view showing a binocular ophthalmoscope embodying the teachings of the present invention.

FIG. 1 illustrates a binocular ophthalmoscope 10, that embodies the teachings of the present invention. The instrument is attached to an arcuate shaped semi-rigid strap 11 by means of a slotted detachable bracket 12 and a threaded fastener 13 that permits the instrument to be rotated about the axis of the fastener and moved in two planes for the purpose of adjusting the instrument in regard to the strap. Once the instrument is properly adjusted at a desired position, the fastener is tightened down to lock the instrument in place. As is well known in the art, the strap is attachable to a head band that permits the instrument to be conveniently worn in front of the examiner's eyes.

Figure 2:
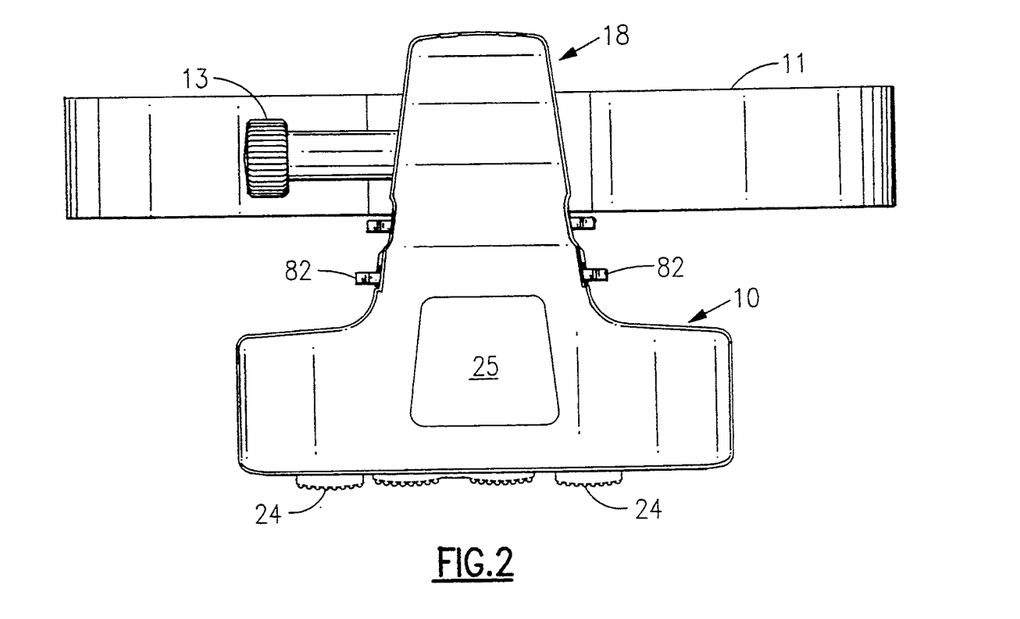
FIG. 2 is an enlarged view showing the binocular ophthalmoscope shown in FIG. 1.
Figures 3, 4:
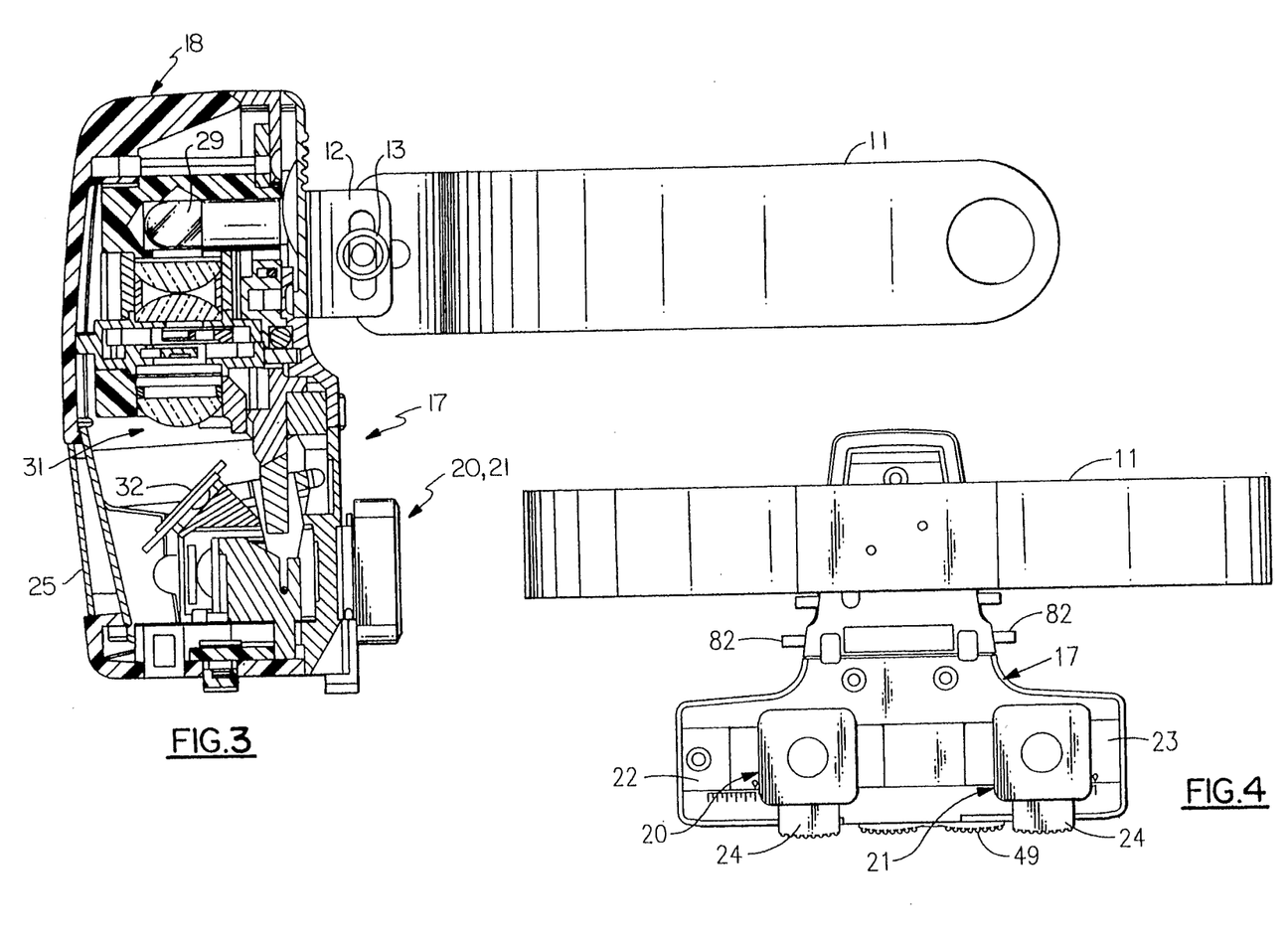
FIGS. 3 is a further enlarged side elevation, in section, showing the binocular ophthalmoscope of FIG. 1.
FIG. 4 is a rear elevation of the binocular ophthalmoscope embodying the present invention.

As further illustrated in FIGS. 2-4 the instrument includes a frame 17 and a housing 18 that is fitted over the frame. A pair of eyepiece units 20 and 21 are slidably mounted in tracks 22 and 23 formed in the frame and are locked in place upon the tracks by means of actuating mechanisms 24-24. The units are arranged to hang below the head strap at eye level and can be laterally positioned by use of the actuating mechanisms to accommodate the wearer. The front of the housing contains a window 25. As will be explained in greater detail below, illumination from an internal light source emanates from the window and is used to illuminate a desired target area inside the patient's eye. Electrical energy is provided to the light source from a battery pack or an A.C. power supply (not shown) via electrical lead 26 (FIG. 1). Images of the illuminated target area are reflected back to the eyepiece units through the window.

As best illustrated in FIG. 3, a high intensity lamp 29 is mounted in the instrument housing 18 and is situated over the frame 17. Light from the lamp is passed through a suitable lens system 31 and is reflected from an illumination mirror 32. The mirror serves to redirect the light beam through the front window 25 of the housing toward the target area inside the eye.

Figure 9:
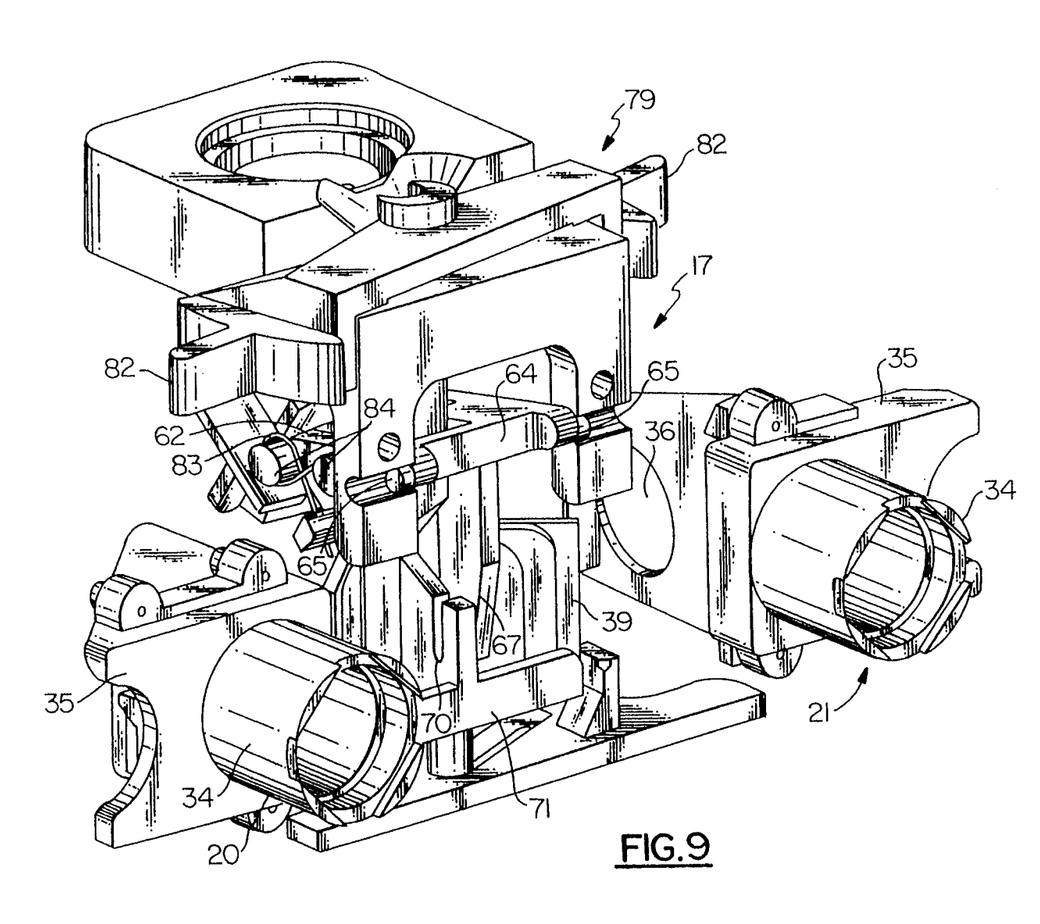
FIG. 9 is a rear perspective view of the main frame assembly embodied in the apparatus of the present invention.
Figure 10:
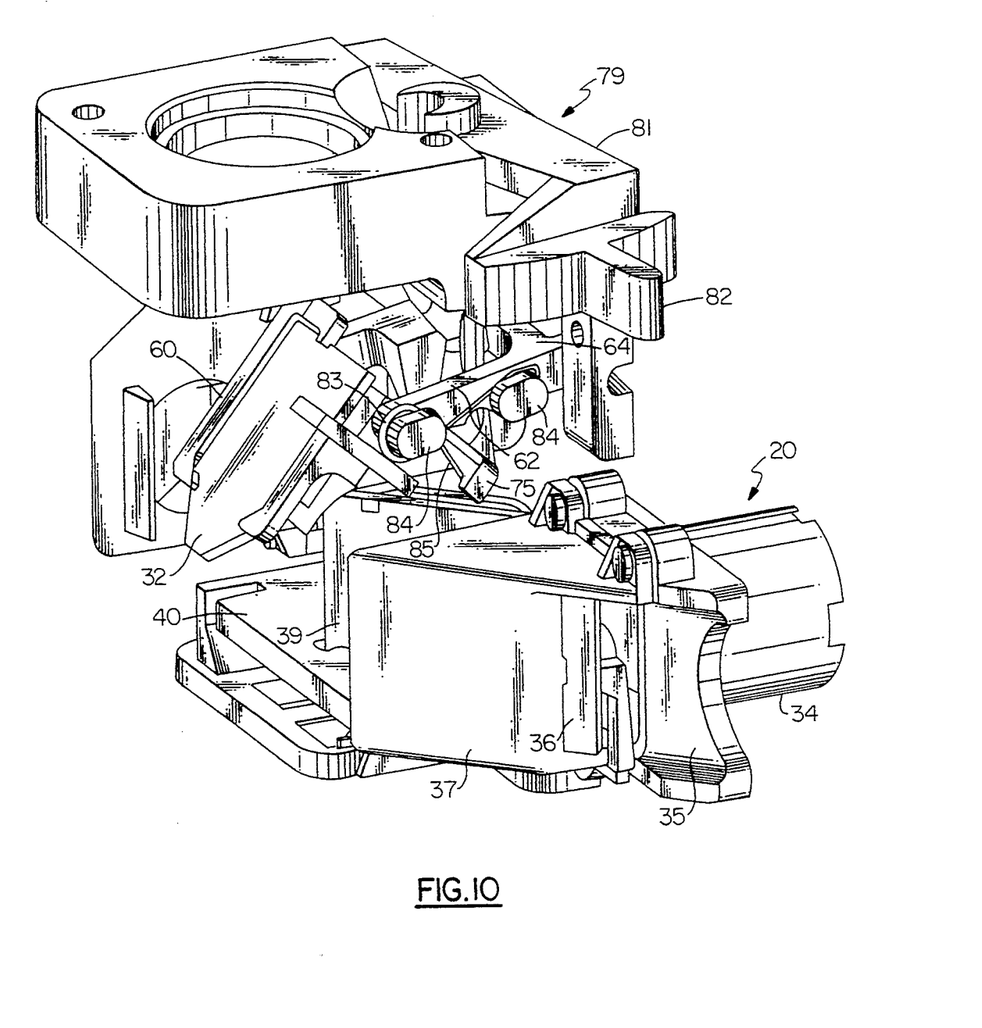
FIG. 10 is a front perspective view of the main frame assembly shown in FIG. 9.
Figure 11:
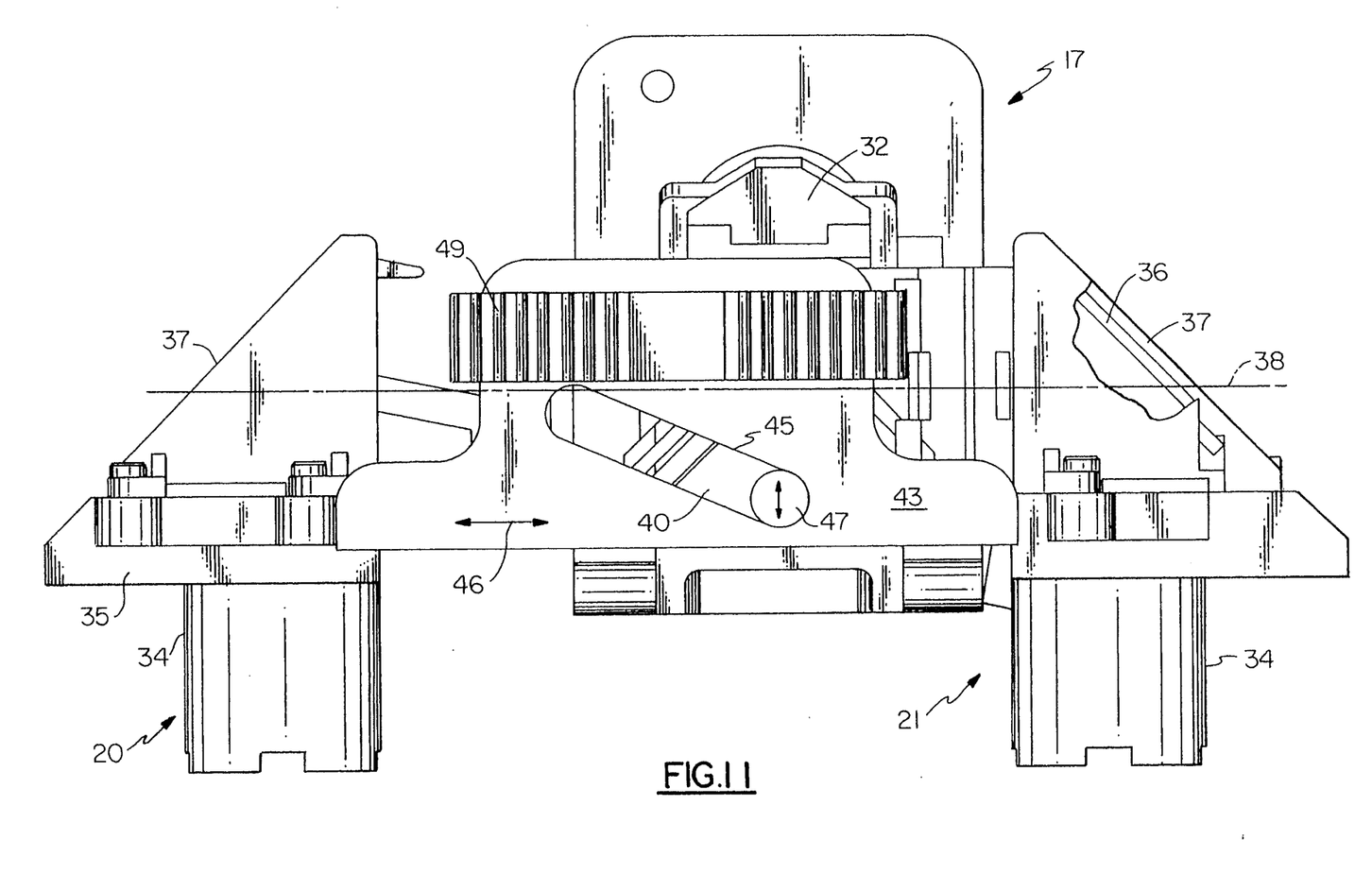
FIG. 11 is a bottom view of the main frame shown in FIG. 9.
Figure 12:
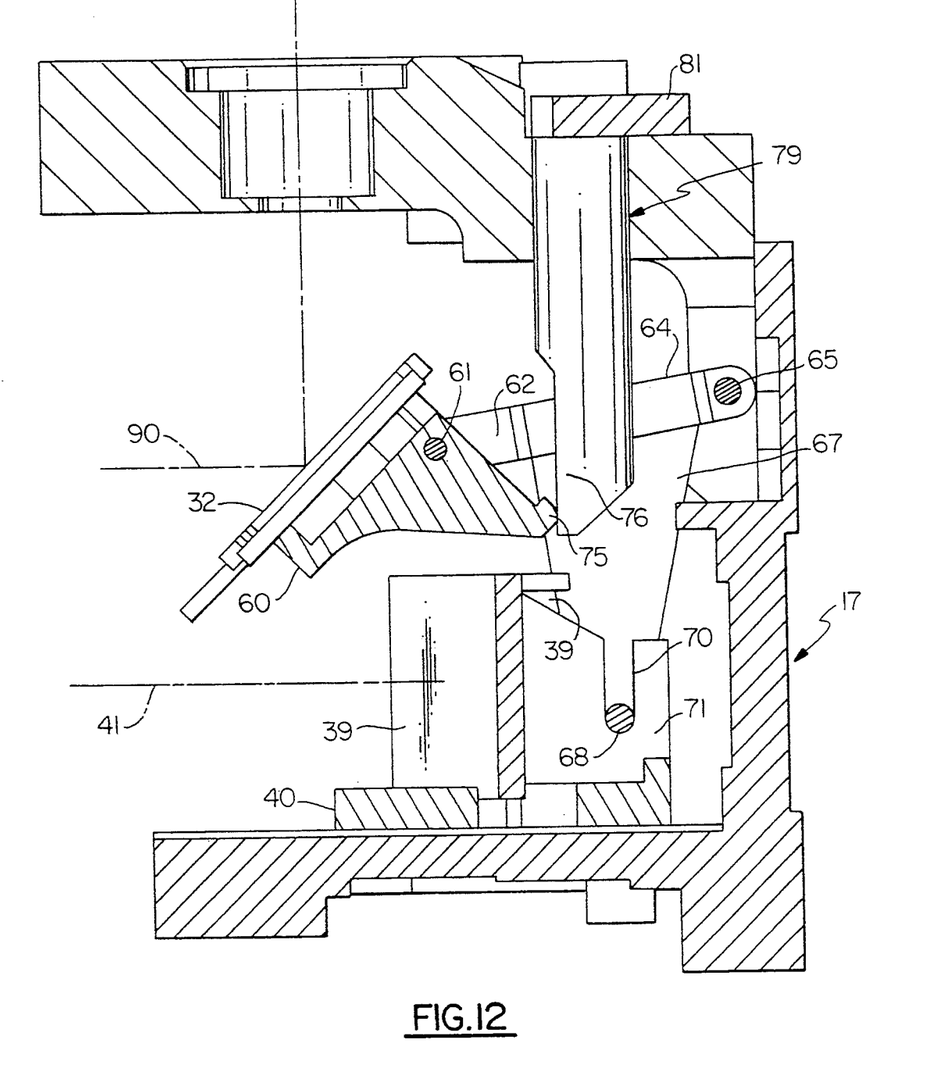
FIG. 12 is a sectional side elevation of the frame shown in FIG. 9 further illustrating the mirror control and adjusting mechanism for the illumination mirror.

Turning now to FIGS. 9-11, the frame 17 of the instrument is shown removed from the housing with pieces broken away to more clearly show the component parts thereof. Each eyepiece unit 20 and 21 contains a lens barrel 34 mounted in support 35. A reflecting surface 36 (FIG. 10) is mounted within a mirror housing 37 directly behind the lens barrel. The reflecting surfaces are mirrors or prisms that turn the optical paths of each eyepiece 90° so that each eyepiece shares a common horizontal viewing axis 38 (FIG. 11). A pair of image reflecting surfaces 39—39 are mounted at right angles upon a movable mirror carriage 40 that is slidably mounted in the frame upon a suitable slide member (not shown). The carriage is directed by the slide member along a reciprocal path of travel that is perpendicular to the common horizontal viewing axis 38 shared by the two eyepieces. Each image reflecting surface makes an angle of 45° with the common viewing axis 38 and thus permits each eyepiece to independently view the target area along separate image paths 41 (FIG. 12). As the carriage is moved toward the target area, the wedge formed by the two image reflecting surfaces causes the two image paths to move apart or diverge. Similarly, moving the carriage away from the target area causes the two image paths to come closer together or converge.

The carriage is operated through means of a slide actuator plate 43 (FIG. 11) which is slidably contained within the frame immediately below the carriage. A canted slotted opening 45 is formed within the actuator plate. A driving pin 47 in the carriage is arranged to pass downwardly into the slotted hole. As indicated by the arrows 46 in FIG. 11, the actuator is arranged to slide laterally in the frame parallel to the common viewing axis 38 of the eyepiece units. This, in turn, moves the driving pin within the slotted hole to reciprocate the carriage along a path of travel perpendicular to the noted common viewing axis. The slide actuator is equipped with finger engageable member 49 that protrudes downwardly below the frame for easy engagement by the examiner.

The previously noted illumination mirror 32 is located above the image reflecting surfaces 39 mounted in the mirror carriage whereby the image reflecting surfaces have an unimpeded view of the target region within an eye undergoing examination. In order to produce effective stereoscopic imaging of objects situated in the back of the eye, the two image paths carrying image data back to the examiner should be separated as far as possible to minimize optical interference and to maximize the stereo effect. By the same token, the light beam entering the eye under examination should also be separated as far as possible from the two image paths to minimize harmful reflections. The size of pupils, however, vary with each patient and can change dramatically if the eye has been dilated. Accordingly, it is extremely important that the examining physician can adjust the distance between the image path axes and the light path axis to maximize the distance therebetween without causing unacceptable parallax.

Figure 5:
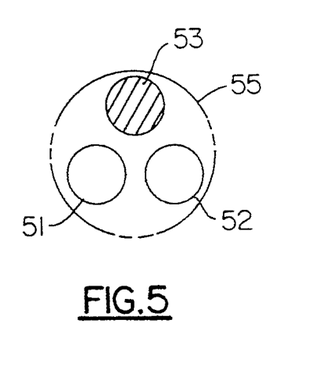
FIGS. 5 and 6 are diagrammatic views showing the positioning of the image paths of the present instrument in relation to its reflected light path.
Figure 6:
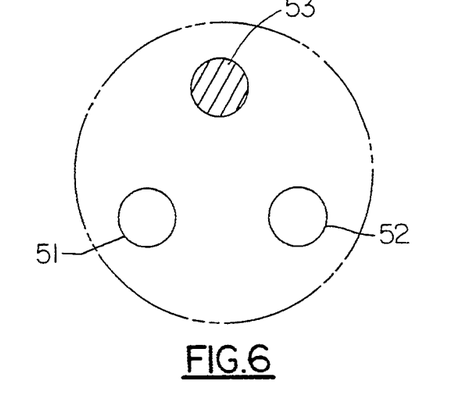

As illustrated in FIG. 5, the positioning of the two image paths 51 and 52 and the light beam 53 must be closely compacted when examining a patient having a small diameter pupil as depicted by the phantom line circle 55. The distance between the image paths and the light path, however, can be increased considerably when examining a patient with a larger pupil or where the eye has been dilated, as illustrated in FIG. 6, to provide for maximum stereoscopic viewing. As noted above, the examiner should be able to make this type of adjustment with the minimum amount of effort and without the light beam interfering with the images reflected back from the target area.

To this end, the illumination mirror is mounted on a tiltable table 60 above the image reflecting surface 39—39 mounted on the reciprocating carriage 40. The table is situated so that it and the mirror supported thereon will not obstruct in any way the ability of the image reflecting surface to see the target area over the full reciprocating range of the carriage. As best shown in FIG. 12, the table is pivotally supported on a pivot pin 61 that is mounted between a pair of arms 62 located at the distal end of yoke 64. The proximal end of the yoke is rotatably secured in the instrument frame 17 by means of trunnions 65—65. Accordingly, the table is afforded two degrees of motion; a first rotational motion as the yoke swings about trunnions 65—65 and a second rocking motion as the table swings about pivot pin 61.

The yoke is secured to an actuating link 67 which includes a stub shaft 68 adapted to ride in a vertically disposed slot 70 formed in control member 71. The control member is securely mounted on the reciprocating carriage between the two image reflecting surfaces. As can be seen, as the carriage moves back and forth over its prescribed path of travel, the yoke is rocked back and forth about the trunnions 65—65.

Figure 7:
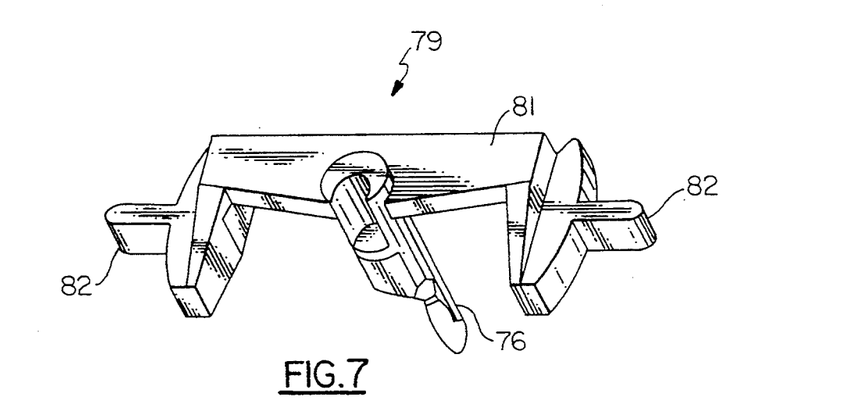
FIGS. 7 and 8 are perspective views showing the camming device for adjusting and controlling the illumination mirror of the present instrument.
Figure 8:
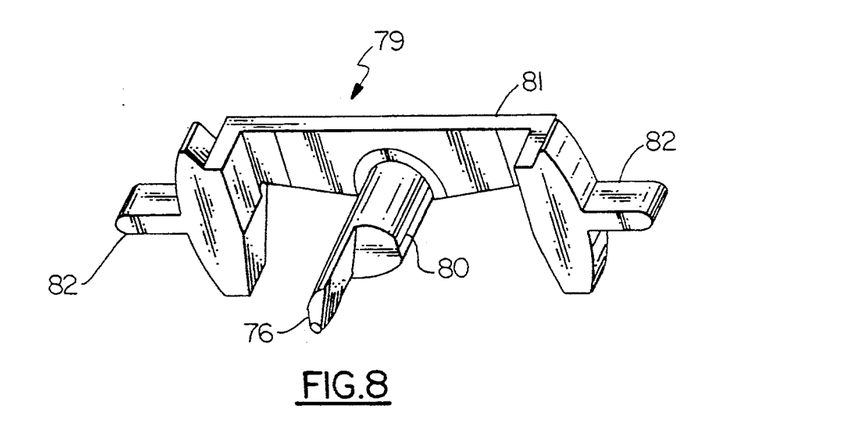

The back of the mirror table 60 as viewed in FIG. 12 has a cam follower 75 attached thereto. The cam follower is arranged to ride in sliding contact with a contoured camming control surface 76 carried on the lower distal end of control rod 79 (See FIGS. 7 and 8). The shank 80 of the control rod is pivotally mounted in the instrument frame 17 and includes a cross arm 81 attached to its upper proximal end of the shank. The cross arm is furnished with a pair of tabs 82—82 that protrude beyond the instrument housing. The tabs are easily accessible to the examiner so that the control rod can be rotationally positioned in the frame.

A spring element 83, (FIG. 10), is mounted on the yoke 64 between two lugs 84—84 with the free end 85 (FIG. 10) of the spring bearing against the cam follower attached to the mirror table 60. The spring serves to urge the cam follower into sliding contact against the contoured camming surface 76 of the control rod 79.

The camming surface of the control rod is profiled circumferentially so as to adjust the tilt of the mirror when the control rod is rotated within the frame. This, in turn, adjusts angular relationship between the light beam axis 90 (FIG. 12) directed by the illumination mirror toward the target area with relation to the axes 41—41 of the two reflected image paths. By simply adjusting the tabs, the examiner is able to direct the light beam into the eye so as to minimize reflected glare and provide for maximum illumination of the target area.

The camming surface is further profiled axially so that the tilt of the mirror table is continually adjusted as the yoke is rocked in response to movement of the carriage. The axial profile is contoured to hold the light beam at the preset angle selected by the examiner as the carriage is moved back and forth within the frame.

As should be evident from the disclosure above, the apparatus of the present invention provides the user with accurate control over the relative positions of the stereoscopic image paths and the illuminating light beam of the instrument by movement of one simple control. This adjustment is herein accomplished without sacrificing or otherwise obstructing the viewing accommodation of the instrument while at the same time allowing for maximum illumination of the image area.

While this invention has been explained with reference to the structure disclosed herein, it is not confined to the details set forth and this invention is intended to cover any modifications and changes as may come within the scope of the following claims:

What is claimed is:

1. A binocular ophthalmoscope for viewing objects inside the eye that includes
    a frame for supporting a pair of opposed eyepieces arranged for viewing along a common horizontal axis,
    a light source for directing a beam of light along a first light path onto an illumination mirror,
    a movable table that supports said illumination mirror in said frame for redirecting a beam of light along a first light path onto an illumination mirror,
    a movable table that supports said illumination mirror in said frame for redirecting the beam of illumination along a second light path for illuminating a target inside the eye,
    a carriage mounted in said frame for reciprocation along a path of travel toward and away from the target,
    a pair of image reflecting surfaces mounted on said carriage for directing images of said target travelling along separate image paths back to each eyepiece so that the distance separating the axes of the image paths move closer together as the carriage is moved toward said target and move further apart as the carriage is moved away from said target and
    control means for angularly adjusting the position of said movable table in response to the movement of said carriage so that the vertical distance separating the axis of the beam of light and the axes of the two image paths decreases as the image paths move closer together and increase as the image paths move further apart.

2. The binocular ophthalmoscope of claim 1 wherein said control means includes a yoke that is rotatingly supported at one end in the frame and said table being pivotally supported in the other end of said yoke, and a link for connecting a lever arm to the carriage.

3. The binocular ophthalmoscope of claim 2 wherein said control means further includes a camming means for regulating the motion of said table as it pivots within said yoke.

4. The binocular ophthalmoscope of claim 3 wherein said camming means further includes an elongated rod mounted for rotation in said frame, a cam means mounted on said rod having a complex camming surface, and a cam follower mounted on said table for following an axially disposed profile on said camming surface as the lever arm is moved by the link whereby the angular relationship of the light beam axis and the axes of the reflected image paths remains constant as the carriage is reciprocated.

5. The binocular ophthalmoscope of claim 4 wherein said cam further includes a second circumferentially disposed profile on said cam means so that the tilt of the mirror table can be independently adjusted by rotating the rod.

6. The binocular ophthalmoscope of claim 5 that further includes a biasing means for urging the cam follower against the cam.

7. The binocular ophthalmoscope of claim 1 that further includes adjusting means for independently positioning each of the eyepiece on said frame.

8. The binocular ophthalmoscope of claim 1 wherein said reflecting surfaces are a pair of orthogonally positioned mirrors or prisms, each of which forms a 45° angle with said common horizontal axis of the two eyepieces.

9. The binocular ophthalmoscope of claim 1 wherein said carriage further includes a driving pin carried in a slide means for reciprocating said carriage.

10. The binocular ophthalmoscope of claim 9 wherein said slide means include a plate slidably mounted in said frame for movement perpendicular to the path of travel of said carriage, said plate having a slotted hole for carrying said driving pin, said slotted hole being angularly offset with regard to the path of travel of said carriage.

11. A method of binocular stereoscopic viewing of a target area inside the eye that includes the steps of directing a light beam from an illumination source along a light axis into a target area inside the eye to illuminate the target area, viewing the illuminated area along two image paths through two perpendicularly disposed reflecting surfaces, moving the reflecting surfaces toward or away from the target area to adjust the horizontal distance separating the axes of the two image paths, independently adjusting the angular orientation of the light beam axis to provide for maximum illumination without harmful reflections, and repositioning the axis of said light beam without disturbing the angular orientation of the light beam axis with respect to the image path axes in response to the movement of the reflecting surfaces.

12. The method of claim 11 that includes the further steps of mounting the reflecting surfaces on a carriage for movement toward and away form the target region, independently mounting a mirror on a movable table for redirecting the light beam from the illumination source into the target area and linking the table to the carriage so that the axis of the light beam is repositioned automatically as the carriage moves toward and away from the target.

* * * * *